US012564360B2

(12) United States Patent
Frach et al.

(10) Patent No.: US 12,564,360 B2
(45) Date of Patent: Mar. 3, 2026

(54) PROCESSING EVENT DATA IN PET IMAGING

(71) Applicant: KONINKLIJKE PHILIPS N.V., Eindhoven (NL)

(72) Inventors: Thomas Frach, Aachen (DE); Oliver Muelhens, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 274 days.

(21) Appl. No.: 18/562,413

(22) PCT Filed: May 26, 2022

(86) PCT No.: PCT/EP2022/064357
§ 371 (c)(1),
(2) Date: Nov. 20, 2023

(87) PCT Pub. No.: WO2022/253694
PCT Pub. Date: Dec. 8, 2022

(65) Prior Publication Data
US 2024/0180500 A1 Jun. 6, 2024

(30) Foreign Application Priority Data
Jun. 3, 2021 (EP) .................................... 21177533

(51) Int. Cl.
*A61B 6/03* (2006.01)
*A61B 6/00* (2024.01)
(Continued)

(52) U.S. Cl.
CPC ............ *A61B 6/037* (2013.01); *A61B 6/4241* (2013.01); *A61B 6/4266* (2013.01);
(Continued)

(58) Field of Classification Search
CPC ..... A61B 6/037; A61B 6/4241; A61B 6/4266; G01T 1/20184; G01T 1/2985; G01T 1/20182; G01T 1/4258
See application file for complete search history.

(56) References Cited

U.S. PATENT DOCUMENTS

| | | |
|---|---|---|
| 2008/0210876 A1 | 9/2008 | Ishitsu et al. |
| 2017/0153337 A1 | 6/2017 | Gao et al. |
| 2019/0268003 A1 | 8/2019 | Loinaz |

FOREIGN PATENT DOCUMENTS

| | | |
|---|---|---|
| CN | 110988960 A | 4/2020 |
| CN | 111815934 A | 10/2020 |

(Continued)

OTHER PUBLICATIONS

Bruschini et al. "SPADnet: a fully digital, scalable, and networked photonic component for time-of-flight PET applications," Proc. SPIE 9129, Biophotonics: Photonic Solutions for Better Health Care IV, 912913 (May 8, 2014).

(Continued)

*Primary Examiner* — Casey Bryant

(57) ABSTRACT

A positron emission tomography imaging system ($100$) includes a plurality of detector elements ($130_{1..i}$) and a plurality of compute elements ($140_{1..j}$). Each compute element ($140_{1..j}$) comprises one or more of the detector elements ($130_{1..i}$), and the compute elements ($140_{1..j}$) are arranged around the bore ($110$) of the PET imaging system. Each compute element ($140_{1..j}$) includes a first communication path ($160_{1..j}$) coupling the compute element to an adjacent compute element in a5circumferential direction around the bore, and a second communication path ($170_{1..j}$) coupling the compute element to a non-adjacent compute element in the circumferential direction. Each compute element ($140_{1..j}$) includes a processor configured to receive the event data generated by its one or more detector elements (Continued)

($130_{1..i}$), and to communicate the event data to the processor of its adjacent compute element, and to the processor of its non-adjacent compute element, via its first communication path10($160_{1..j}$), and via its second communication path ($170_{1..j}$), respectively.

15 Claims, 5 Drawing Sheets

(51) Int. Cl.
  *A61B 6/42* (2024.01)
  *G01T 1/20* (2006.01)
  *G01T 1/29* (2006.01)
(52) U.S. Cl.
  CPC ........ *A61B 6/4411* (2013.01); *G01T 1/20184* (2020.05); *G01T 1/2985* (2013.01)

(56)          References Cited

FOREIGN PATENT DOCUMENTS

| EP | 3276381 A1 | 1/2018 | |
|----|------------|--------|---|
| EP | 4098200 A1 * | 12/2022 | ........... A61B 6/4411 |

OTHER PUBLICATIONS

Veerappan et al., "Sensor network architecture for a fully digital and scalable SP AD based PET system", 2012 IEEE Nuclear Science Symposiwn and Medical Imaging Conference Record (NSS/MIC), pp. 1115-1118, Downloaded on Feb. 2, 2021.
Garzetti et al., "Plug-and-play TOF-PET Module Readout Based on TDC-on-FPGA and Gigabit Optical Fiber Network".
International Search report and Written Opinion of PCT/EP2022/064357, dated Jul. 21, 2022.

* cited by examiner

PROCESSING EVENT DATA IN PET IMAGING

CROSS-REFERENCE TO PRIOR APPLICATIONS

This application is the U.S. National Phase application under 35 U.S.C. § 371 of International Application No. PCT/EP2022/064357, filed on May 26, 2022, which claims the benefit of European Patent Application No. 21177533.3, filed on Jun. 3, 2021. These applications are hereby incorporated by reference herein.

TECHNICAL FIELD

The present disclosure relates to the processing of event data in a positron emission tomography, PET, imaging system.

BACKGROUND

PET imaging systems are used to study biological processes within the anatomy by means of a radiotracer. A radiotracer is typically attached to a molecule such as glucose or a ligand, and injected into the bloodstream of a subject. The bloodstream circulates the radiotracer within the anatomy, and the radiotracer is preferentially absorbed, or "uptaken" in certain regions depending on the region's biological function and depending on the attachment molecule. PET images representing the spatial distribution of the radiotracer within the anatomy are then generated using the PET imaging system. A clinician may study such images in order to make a diagnosis of the subject.

The spatial distribution of a radiotracer within the anatomy is determined by detecting gamma quanta that are emitted by the radiotracer whilst it decays. As the radiotracer decays, it emits positrons. The positrons are annihilated locally by electrons, resulting in the simultaneous emission of pairs of oppositely-directed gamma quanta. The emission of each pair of gamma quanta may be referred-to as a radioactive decay event, or simply an "event".

In order to detect the gamma quanta, a PET imaging system includes multiple detector elements. The detector elements are arranged around a bore of the imaging system in order to detect the gamma quanta emitted from a portion of a subject within the bore. The detector elements include scintillator arrays that are coupled to photodetector arrays. Each time a gamma quant is received by a detector element, scintillation light is generated in a scintillator array, and the scintillation light is detected by its corresponding photodetector array. The detection times of the received gamma photons, often referred-to as "timestamps" and/or the light distribution generated in the scintillator array in response to the received gamma quanta, are referred-to as radioactive decay event data, or simply, "event data". The event data generated by the detector elements is processed in order to localize the origin of each event within the bore.

Processing the event data may involve an initial step of analyzing the scintillation light distribution that is detected by the photodetector array in response to each received gamma quant, and assigning the light distribution to a common received gamma quant; a process referred-to as "clustering". Clustering is performed in order to determine the most likely location on the detector at which each gamma quant was received and/or to determine the energy of the received gamma quant.

Processing the event data may also involve comparing the detection times of the received gamma photons in order to identify pairs of gamma quanta that are received within a predetermined time interval of one another; a process referred-to as "coincidence search". In coincidence search, pairs of gamma quanta that are received within a predetermined time interval of one another that is defined by the bore diameter and the speed of travel of a gamma photon, are assumed to have originated from a common radioactive decay event. Such pairs of gamma quanta are referred-to as "coincident pairs", and define a line of response, or "LOR" between the locations on the detectors at which they are detected. Under this assumption, a LOR intercepts the origin of the decay event, but its position along the LOR is uncertain. In so-called time-of-flight "TOF" PET imaging, a more accurate position of the actual decay event along the LOR may be determined based on a time difference between the times of detection of the gamma quanta in each coincident pair. The LORs from multiple decay events are used to reconstruct a PET image representing the distribution of the radiotracer in the subject.

The processing of event data in PET imaging systems is extremely intensive in view of the need to determine the event data for individual gamma quanta, and the rate at which the gamma quanta are received. The image quality of the resulting PET images is determined in-part by the accuracy and the rate at which the origins of each coincident pair can be determined. Consequently, in PET imaging systems, the operations of coincidence search, and clustering, are typically performed by a common, central, processor.

A document by Bruschini, C., et al, entitled "SPADnet: a fully digital, scalable, and networked photonic component for time-of-flight PET applications" published in Biophotonics: Photonic Solutions for Better Health Care IV, edited by Jürgen Popp, Valery V. Tuchin, Dennis L. Matthews, Francesco S. Pavone, Proc. of SPIE Vol. 9129, 912913 discloses a sensor tile interfaced to an FPGA-based PCB on its back. The resulting photonic module acts as an autonomous sensing and computing unit, individually detecting gamma photons as well as thermal and Compton events. It determines in real time basic information for each scintillation event, such as exact time of arrival, position and energy, and communicates it to its peers in the field of view. Coincidence detection therefore occurs directly in the ring itself, in a differed and distributed manner to ensure scalability. The selected true coincidence events are then collected by a snooper module, from which they are transferred to an external reconstruction computer using Gigabit Ethernet.

However, there remains room to provide an improved processing architecture for processing event data in PET imaging systems.

SUMMARY

According to one aspect of the present disclosure, a PET imaging system, is provided. The PET imaging system includes: a bore for receiving a subject, the bore comprising an axis; a plurality of detector elements; and a plurality of compute elements. Each detector element comprises a scintillator array coupled to a photodetector array, and is configured to generate event data in response to received gamma quanta. The event data represent detection times of the received gamma quanta and/or a light distribution generated in the scintillator array in response to the received gamma quanta. Each compute element comprises one or more of the detector elements. The compute elements are arranged around the axis of the bore such that the detector elements generate the event data in response to gamma quanta received from within the bore. Each compute element comprises a first communication path coupling the compute element to an adjacent compute element in a circumferential direction around the bore, and a second communication path coupling the compute element to a non-adjacent compute element in the circumferential direction. Each compute element comprises a processor configured to receive the event data generated by its one or more detector elements, and to communicate the event data to the processor of its adjacent compute element, and to the processor of its non-adjacent compute element, via its first communication path, and via its second communication path, respectively.

Further aspects, features, and advantages of the present disclosure will become apparent from the following description of examples, which is made with reference to the accompanying drawings.

DETAILED DESCRIPTION

Figures 1, 2:
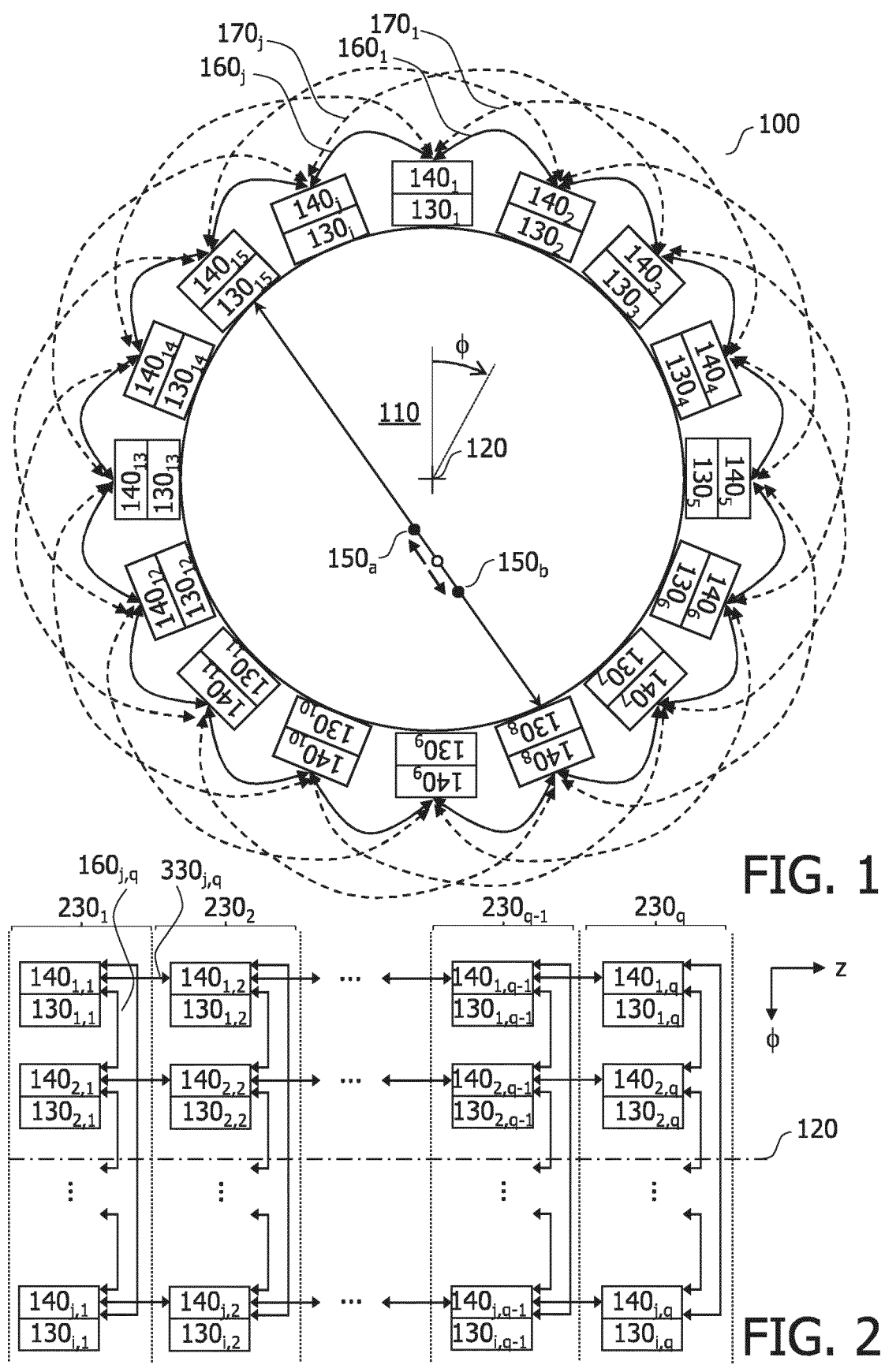
FIG. 1 is a schematic diagram illustrating an example PET imaging system 100 including a plurality of compute elements $140_{1..j}$, in accordance with some aspects of the present disclosure.
FIG. 2 is a schematic diagram illustrating an example PET imaging system 100 including a plurality of compute elements $140_{1..j,1..q}$ that are arranged in a plurality of rings $230_{1..q}$, in accordance with some aspects of the present disclosure.

Examples of the present disclosure are provided with reference to the following description and figures. In this description, for the purposes of explanation, numerous specific details of certain examples are set forth. Reference in the specification to "an example", "an implementation" or similar language means that a feature, structure, or characteristic described in connection with the example is included in at least that one example. It is also to be appreciated that features described in relation to one example may also be used in another example, and that all features are not necessarily duplicated in each example for the sake of brevity.

In the following description, reference is made to a PET imaging system. It is to be appreciated that the PET imaging system may be any type of PET imaging system, including a time-of-flight "TOF" PET imaging system, and a non-TOF-PET imaging. Reference is made to examples of PET imaging systems that include multiple detector elements. The detector elements are arranged in one or more rings that are disposed axially along the axis of a bore of the PET imaging system. In some examples, the axial extent of the rings is sufficient to cover a substantial portion, or even the entire length, of a human subject. Some examples of the present disclosure may therefore be used in so-called "full-body" PET imaging systems. However, it is to be appreciated that some examples of the present disclosure may, as appropriate, be used with PET imaging systems that include only a single ring of detector elements.

In the following description, reference is made to a processor. In some examples, the processor forms part of a compute element. The processor carries out various methods, which may thus be referred-to as computer-implemented methods. In this respect, it is noted that the computer-implemented methods may be provided as a non-transitory computer-readable storage medium including computer-readable instructions stored thereon, which, when executed by at least one processor, cause the at least one processor to perform the method. In other words, the computer-implemented methods may be implemented in a computer program product. The computer program product can be provided by dedicated hardware, or hardware capable of running the software in association with appropriate software. When provided by a processor, the functions of the method features can be provided by a single dedicated processor, or by a single shared processor, or by a plurality of individual processors, some of which can be shared.

The explicit use of the terms "processor" or "controller" should not be interpreted as exclusively referring to hardware capable of running software, and can implicitly include, but is not limited to, digital signal processor "DSP" hardware, read only memory "ROM" for storing software, random access memory "RAM", a non-volatile storage device, and the like. Furthermore, examples of the present disclosure can take the form of a computer program product accessible from a computer-usable storage medium, or a computer-readable storage medium, the computer program product providing program code for use by or in connection with a computer or any instruction execution system. For the purposes of this description, a computer-usable storage medium or a computer readable storage medium can be any apparatus that can comprise, store, communicate, propagate, or transport a program for use by or in connection with an instruction execution system, apparatus, or device. The medium can be an electronic, magnetic, optical, electromagnetic, infrared, or a semiconductor system or device or propagation medium. Examples of computer-readable media include semiconductor or solid state memories, magnetic tape, removable computer disks, random access memory "RAM", read-only memory "ROM", rigid magnetic disks and optical disks. Current examples of optical disks include compact disk-read only memory "CD-ROM", compact disk-read/write "CD-R/W", Blu-Ray™ and DVD.

As mentioned above, the processing of event data in PET imaging systems is extremely intensive in view of the need to determine the event data for individual gamma quanta, and the rate at which the gamma quanta are received. The image quality of the resulting PET images is determined in-part by the accuracy and the rate at which the origins of each coincident pair can be determined. Consequently, in PET imaging systems, the operations of coincidence search, and clustering, are typically performed by a common, centralized, processor.

FIG. 1 is a schematic diagram illustrating an example PET imaging system 100 including a plurality of compute elements 140$_{1..j}$, in accordance with some aspects of the present disclosure. The PET imaging system 100 illustrated in FIG. 1 includes a a bore 110 for receiving a subject. The bore 110 has an axis 120, which extends into the plane of the illustration. In-use, the bore 110 may receive a subject, such as a human body, along the axis 120, by means of a patient bed (not illustrated). The patient bed may be extended into the bore 110 in order to perform a PET imaging procedure on the subject. The PET imaging procedure may be used to detect a distribution of a radiotracer within a region of interest in the subject. A radiotracer such as $^{18}$F-fluoro-2-deoxy-D-glucose "FDG", or another radiotracer, may have been previously injected into the subject for this purpose. The region of interest may be a particular organ, such as the heart, the brain, the lungs, and so forth, or a substantial portion of the body in a so-called "full-body" PET scan.

The PET imaging system 100 illustrated in FIG. 1 also includes multiple detector elements 130$_{1..i}$. Each detector element 130$_{1..i}$ comprises a scintillator array (not illustrated) coupled to a photodetector array (not illustrated), and is configured to generate event data in response to received gamma quanta, such as the gamma quanta 150$_a$, 150$_b$ illustrated in FIG. 1. The event data represent detection times of the received gamma quanta 150$_a$, 150$_b$ and/or a light distribution generated in the scintillator array in response to the received gamma quanta 150$_a$, 150$_b$. The scintillator array may be formed from various scintillator materials that generate scintillation light in response to received gamma quanta. Scintillator materials such as lutetium yttrium orthosilicate "LYSO", bismuth germanate "BGO", and garnets such as gadolinium aluminium gallium garnet "GAGG", and so forth, are known for this purpose. The photodetector array may be formed from various materials that are suitable for detecting the scintillation light. A silicon photodetector array that includes a plurality of silicon avalanche photodiodes may for example be used for this purpose. The photodetector array is optically coupled to the scintillator array such that the spatial distribution of the scintillation light that is generated in the scintillator array in response to received gamma quanta, is measured by the photodetector array. The photodetector array may be coupled to readout electronics for generating the event data from electrical signals generated by the photodetector array. The detector elements may be supplied with a clock signal for synchronizing the event data with the event data generated by other detector elements, thereby providing accurate measurements of the detection times. In some examples, the detector elements may also include a buffer for storing the event data.

As illustrated in FIG. 1, each compute element 140$_{1..j}$ includes one or more of the detector elements 130$_{1..i}$. Moreover, the compute elements 140$_{1..j}$ are arranged around the axis 120 of the bore 110 such that the detector elements 130$_{1..i}$ generate the event data in response to gamma quanta 150$_a$, 150$_b$ received from within the bore 110. In this respect, the gamma radiation-receiving faces of the detector elements 130$_{1..i}$ are oriented towards the bore 110. In some examples, the detector elements 130$_{1..i}$ are arranged such that their gamma radiation-receiving faces are perpendicular to a line extending from the axis 120 to the center of the gamma radiation-receiving faces of the detector elements 130$_{1..i}$. The detector elements 130$_{1..i}$ may consequently each be located around a circumference of a circle that is co-axial with the axis 120 of the bore 110. In other examples, the gamma radiation-receiving faces of the detector elements 130$_{1..i}$ may be aligned with the edges of a polygon and arranged around the axis 120. For example, the gamma radiation-receiving faces of the detector elements 130$_{1..i}$ may be aligned with the edges of a regular n-sided polygon having a center that is coaxially aligned with the axis 120 of the bore 110, and wherein n is equal to 3 or more. The gamma radiation-receiving faces of one or more of the detector elements 130$_{1..i}$ may be aligned with each edge of such an regular n-sided polygon. In such an arrangement the detector elements 130$_{1..i}$ may be said to be arranged transaxially with respect to the axis 120. In other examples, the detector elements 130$_{1..i}$ may be arranged around the axis 120 of the bore 110 in a different manner. For example, the detector elements 130$_{1..i}$ may be arranged around the outer surface of an oval shape, or another shape. In some examples, the detector elements 130$_{1..i}$ may include gaps of varying size between them. In one example, the detector elements 130$_{1..i}$ may be arranged around the axis 120 by disposing the detector elements 130$_{1..i}$ on two or more planes that oppose one another across the axis of the bore.

As also illustrated in FIG. 1, each compute element 140$_{1..j}$ includes a first communication path 160$_{1..j}$ coupling the compute element to an adjacent compute element in a circumferential direction around the bore, and a second communication path 170$_{1..j}$ coupling the compute element to a non-adjacent compute element in the circumferential direction. The communication paths may in general be electrical or optical communication paths. The angle f in FIG. 1 represents the circumferential direction. Thus, as illustrated by the example in FIG. 1, the compute element 140$_1$ has a first communication path 160$_1$ to adjacent compute element 140$_2$ in the clockwise circumferential direction, f, and a second communication path 170$_1$ to the non-adjacent compute element 140$_4$ in the clockwise circumferential direction, f. The non-adjacent compute element may in general be two or more compute elements away in the circumferential direction, i.e. the closest non-adjacent compute element to the compute element 140$_1$ would be two compute elements away, i.e. compute element 140$_3$.

Moreover, each compute element 140$_{1..j}$ includes a processor (not illustrated) that is configured to receive the event data generated by its one or more detector elements 130$_{1..i}$, and to communicate the event data to the processor of its adjacent compute element, and to the processor of its non-adjacent compute element, via its first communication path 160$_{1..j}$, and via its second communication path 170$_{1..j}$, respectively.

In comparison to a conventional PET processing architecture that uses a central processor to process the event data generated by the detector elements, i.e. the detection times of the received gamma quanta $150_a$, $150_b$ and/or a light distribution generated in the scintillator array in response to the received gamma quanta $150_a$, $150_b$, the distributed processing architecture illustrated in FIG. 1 alleviates the problem that a central processing unit has to be capable of handling the combined data rate arising from the events from all detector elements. The distributed processing architecture illustrated in FIG. 1 therefore permits the use of lower speed processors for processing the event data because the individual processors may operate temporally in parallel. The first communication path $160_{1..j}$ between adjacent detector elements permits the transfer of the event data from a compute element to its adjacent compute element. The second communication path $170_{1..j}$ between a compute element and a non-adjacent compute element permits the transfer of event data to a compute element that is further away around the bore 110. Both communication paths may also be used to exchange handshake data. In PET imaging systems, the coincident pairs of oppositely-directed gamma quanta are typically detected on opposite sides of the bore 110. The second communication path $170_{1..j}$ between a compute element and a non-adjacent compute element therefore provides a faster, i.e. reduced latency, communication path around the bore 110 between the expected detection positions of coincident gamma. By obviating the need to transfer event data around the bore via every single compute element along the path, improved PET imaging system performance, is provided. In-use, the processors may dynamically select which of the first and second communication paths to use when communicating the event data. The path may for example be selected based on one or more factors such as the shortest distance between the origin and the destination of the event data, the current utilization of the available communication paths; for example the path that provides the shortest latency, and the rate at which gamma quanta are detected. In some examples, the criterion, or criteria, for selecting the path may also change over time, depending for example on the rate at which gamma quanta are detected, whether a path is blocked or missing due to a fault, the path with the shortest latency and so forth.

In some examples, the compute elements may also include a buffer (not illustrated) for storing the event data. The buffer may be used to store the event data prior to its transfer to another compute element. In order to prevent that the buffer becomes overloaded, the event data may be discarded by the buffer if no corresponding event is detected within an expiration time after the event enters the buffer. In one example, the expiration time may be adjusted dynamically, i.e. in real-time. The expiration time may for example be dependent on the rate at which gamma quanta are detected. The effect of this is a dynamic adaptation of the acceptance angle.

The PET imaging system described above may include one or more additional features. These are described below with reference to further examples. It is noted that whilst the examples may be described individually, these examples may also be combined to provide further advantageous effects.

In one example, the processor of each compute element $140_{1..j}$, $140_{1..j,1..q}$ clusters the event data and/or identifies coincident pairs. In this example, the processor of each compute element $140_{1..j}$, $140_{1..j,1..q}$ is further configured to:

cluster the event data by assigning the light distribution generated in one or more scintillator arrays to a common received gamma quant $150_a$, $150_b$; and/or identify coincident pairs of received gamma quanta $150_a$, $150_b$ having detection times within a predetermined time interval of one another.

The first and second communication paths $160_{1..j}$, $170_{1..j}$ provide efficient routing of the event data between the compute elements, thereby permitting the clustering and/or identifying operations to be performed by the compute elements in an efficient manner.

The processor of each compute element $140_{1..j}$, $140_{1..j,1..q}$ clusters the event data by assigning the light distribution generated in one or more scintillator arrays of a detector element $130_{1..i}$, $130_{1..i,1..q}$ of the compute element $140_{1..j}$, $140_{1..j,1..q}$, and/or the light distribution generated in one or more scintillator arrays of a detector element $130_{1..i}$, $130_{1..i,1..q}$ of an adjacent compute element $140_{1..j}$, $140_{1..j,1..q}$, to a common received gamma quant $150_a$, $150_b$. This operation may be carried out based on the detection times of portions of the light distribution by the photodetectors in the array, together with the expected lateral spread of the light distribution from a gamma quant. The processor of each compute element $140_{1..j}$, $140_{1..j,1..q}$ may compute a total energy of the received gamma quant $150_a$, $150_b$ based on the cluster. This operation may be carried out by integrating the light distribution for the cluster, or counting the individual number scintillation light photons that are generated. The photodetector array may include an electrical integrating circuit, or a so-called photon counting detector for these purposes respectively. The processor of each compute element $140_{1..j}$, $140_{1..j,1..q}$ may determine a position of the received gamma quant $150_a$, $150_b$ based on the cluster. The processor may determine the position of the received gamma quant $150_a$, $150_b$ by computing the centroid of the light distribution for a cluster, for example.

In one example, the total energy of the gamma quant may be compared to an expected energy of the gamma quanta emitted by the radiotracer during its decay in order to distinguish between true coincidence events, and scattered coincidence events. If the total energies of both gamma quanta in the coincident pair are within a predetermined range of the expected energy, the coincident pair may be labelled as a "true coincidence" event. If the total energy of one or both gamma quanta in the coincident pair are outside the predetermined range, the coincident pair may be labelled respectively as a "scattered coincidence" event or a "scatter event". Scatter events may be used to correct the true coincidence events, or omitted from use in PET image reconstruction.

In one example, the processor of each compute element $140_{1..j}$, $140_{1..j,1..q}$ may identify coincident pairs of received gamma quanta $150_a$, $150_b$ having detection times within a predetermined time interval of one another by:

comparing the detection time of a gamma quant $150_a$, $150_b$ detected by a detector element $130_{1..i}$, $130_{1..i,1..q}$ of the compute element $140_{1..j}$, $140_{1..j,1..q}$, with the detection times of one or more other gamma quanta $150_a$, $150_b$ detected by other detector elements $130_{1..i}$, $130_{1..i,1..q}$ of other compute elements $140_{1..j}$, $140_{1..j,1..q}$ to identify a corresponding gamma quant $150_a$, $150_b$ having a detection time within the predetermined time interval.

Having identified a coincident pair of gamma quanta, one of the processors may then transmit the event data for its gamma quant to the processor of the corresponding gamma quant in the pair. Thus, in one example, the processor of each compute element $140_{1..j}$, $140_{1..j,1..q}$ may further:

identify, based on the comparing, a corresponding compute element $140_{1..j}$, $140_{1..j,1..q}$ of the detector element $130_{1..i}$, $130_{1..i,1..q}$ detecting the corresponding gamma quant; and transmit the event data of the detected gamma quant $150_a$, $150_b$ to the processor of the corresponding compute element $140_{1..j}$, $140_{1..j,1..q}$, and/or receive the event data of the corresponding gamma quant $150_a$, $150_b$ from the other compute element $140_{1..j}$, $140_{1..j,1..q}$.

In one example, the processor of each compute element $140_{1..j}$, $140_{1..j,1..q}$ may further communicate the event data for coincident pairs to i) a computer readable storage medium and/or ii) a reconstruction processor 200. The reconstruction processor may reconstruct a PET image representing the distribution of radiotracer in the subject using the received event data.

As mentioned above, in some examples, the compute elements of the detector elements that detect a coincident pair of gamma quanta may operate as both transmitters and receivers of their event data. Thus, in these examples, the processor of each compute element $140_{1..j}$, $140_{1..j,1..q}$ may transmit the event data generated by its one or more detector elements $130_{1..i}$, $130_{1..i,1..q}$ to the processor of its adjacent compute element $140_{1..j}$, $140_{1..j,1..q}$ and to the processor of its non-adjacent compute element $140_{1..j}$, $140_{1..j,1..q}$ via its first communication path and via its second communication path, respectively. The processor of each compute element $140_{1..j}$, $140_{1..j,1..q}$ may also receive event data from the processor of its adjacent compute element $140_{1..j}$, $140_{1..j,1..q}$, and from the processor of its non-adjacent compute element $140_{1..j}$, $140_{1..j,1..q}$ via its first communication path and via its second communication path, respectively.

This protocol may however lead to inefficient use of the compute elements since there is a risk that the event data from a coincident pair of gamma quanta is processed by both of their respective compute elements. In order to obviate this risk, the event data from the coincident pairs of gamma quanta may be filtered based on a comparison of their detection times in order to remove duplicated events.

In some examples, it is also contemplated to designate the compute elements of detector elements that receive the gamma quanta as transmitters or receivers of the event data using a control signal. Thus, in one example, each compute element $140_{1..j}$, $140_{1..j,1..q}$ is further configured to receive a control signal for switching operation of each compute element $140_{1..j}$, $140_{1..j,1..q}$ between i) transmitting the event data generated by its one or more detector elements $130_{1..i}$, $130_{1..i,1..q}$ to the processor of its adjacent compute element $140_{1..j}$, $140_{1..j,1..q}$ and to the processor of its non-adjacent compute element $140_{1..j}$, $140_{1..j,1..q}$, and ii) receiving event data from the processor of its adjacent compute element $140_{1..j}$, $140_{1..j,1..q}$, and from the processor of its non-adjacent compute element $140_{1..j}$, $140_{1..j,1..q}$.

In one example, the control signal may be used to make a designation of the role of each compute element as a transmitter or receiver of event data. For example, odd-numbered compute elements $140_j$ around the bore 110 may be designated as transmitters of their event data, and even-numbered compute elements $140_j$ around the bore 110 may be designated as receivers of event data from other compute elements. A static designation of the roles of the compute elements may, however result in poor balancing of the processing load amongst the compute elements. It also risks that corresponding event data that is detected by two transmitters, or two receivers, fails to be matched. In order to address these two issues, in one example, the control signal may be used to dynamically switch the designation of each compute element between a transmitter or receiver of event data. A buffer may be used to store the event data, as mentioned above. When the roles of the compute elements are switched, the data from both transmitters, or both receivers, can be transferred between the compute elements from the buffers. The dynamic switching may of the roles may be performed periodically, or based on the current processing load of a compute element, for example.

This approach, however incurs the risk that events that are detected close to the transition of the designations of the compute elements, are missed. Thus, in one example, the control signal may be used to dynamically switch the designation of each compute element between a transmitter and a receiver of event data such that the designation of the compute elements are switched at different times. Compute elements may then discard duplicated events based on a comparison of the detection times of the transmitted and received events.

FIG. 1 illustrated an example PET imaging system 100 including a plurality of compute elements $140_{1..j}$. The compute elements may be said to be arranged around the bore in a "ring". As an alternative to the single ring illustrated in FIG. 1, it is also contemplated to arrange the compute elements in multiple rings. FIG. 2 is a schematic diagram illustrating an example PET imaging system 100 including a plurality of compute elements $140_{1..j,1..q}$ that are arranged in a plurality of rings $230_{1..q}$, in accordance with some aspects of the present disclosure. In FIG. 2, the rings $230_{1..q}$ are distributed axially along the axis 120 of the bore 110. The use of multiple rings in this manner extends the axial field of view of the PET imaging system 100. Moreover, the processor of each compute element $140_{1..j,1..q}$ in a ring $230_{1..q}$ is further configured to communicate the event data to the processor of an adjacent compute element in an adjacent ring. The compute elements $140_{1..j,1..q}$ illustrated in FIG. 2, each include an example third communication path $330_{j,q}$ for this purpose. In so doing, the compute elements may process event data from coincident pairs of gamma quanta when the gamma quanta are received by detector elements in different rings. This may improve the sensitivity of the PET imaging system.

The example PET imaging system illustrated in FIG. 2 may have two or more rings. Thus, the index q in FIG. 2 which indicates the ring number, may be equal to two or more. The use of multiple rings provides a longer axial field of view of the PET imaging system without needing to translate the subject relative to the PET imaging system along the axis of the bore in order to generate a PET image. In the arrangement illustrated in FIG. 2, event data can be transferred between different compute elements $140_{1..j,1..q}$ within a ring via the first communication path $160_1$ and via the second communication path $170_1$, as described above in relation to FIG. 1, as well as between different rings via the third communication path $330_{j,q}$. For ease of illustration, in FIG. 2, only the first communication path $160_{j,q}$ between adjacent compute elements within a ring, and the third communication path $330_{j,q}$ between adjacent compute elements in adjacent rings, are illustrated.

Instead of, or in addition to, the third communication path $330_{j,q}$ illustrated in FIG. 2, the compute elements $140_{j,q}$ may for example include one or more communication paths to non-adjacent compute elements in adjacent rings.

Figure 3:
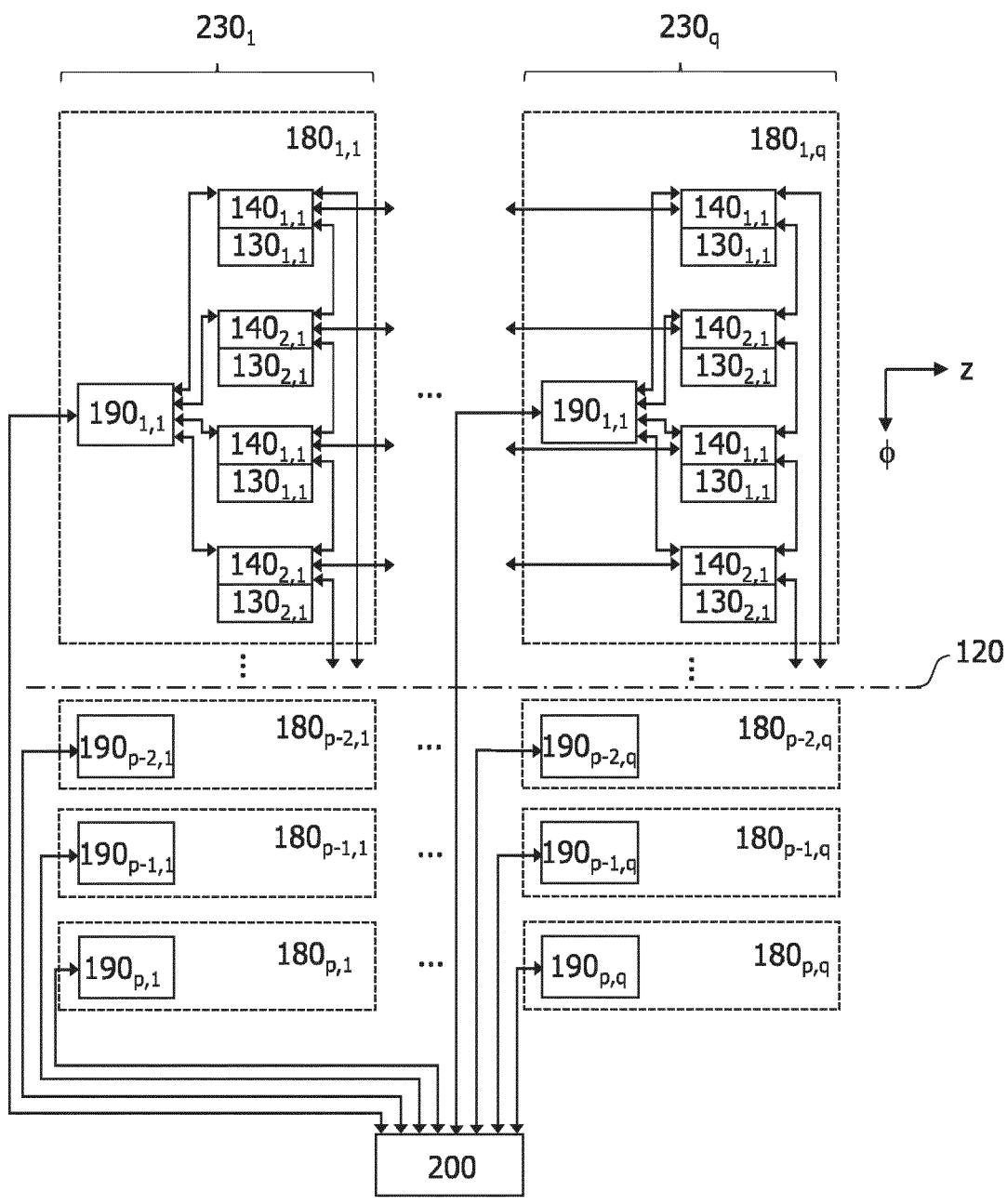
FIG. 3 is a schematic diagram illustrating the grouping of a plurality of compute elements $140_{1..j,1..q}$ in order to define a plurality of module elements $180_{p,q}$, in accordance with some aspects of the present disclosure.

In some examples, multiple compute elements are grouped together in module elements. FIG. 3 is a schematic diagram illustrating the grouping of a plurality of compute elements $140_{1..j,1..q}$ in order to define a plurality of module elements $180_{p,q}$, in accordance with some aspects of the present disclosure. The grouping of the compute elements is illustrated in FIG. 3 for multiple rings, q, but a similar grouping of the compute elements into module elements may also be used in an alternatively arrangement with a single ring. Each module element $180_{p,q}$ includes a plurality of the compute elements $140_{1..j}$, $140_{1..j,1..q}$ and a transceiver $190_{p,q}$. The transceiver $190_{p,q}$ of each module element $180_{p,q}$ is in communication with the compute elements $140_{1..j}$, $140_{1..j,1..q}$ of the module element $180_{p,q}$, and configured to receive the event data generated by the one or more detector elements $130_{1..i}$, $130_{1..i,1..q}$ of the compute elements $140_{1..j}$, $140_{1..j,1..q}$ of the module element $180_{p,q}$. The transceiver $190_{p,q}$ of each module element $180_{p,q}$ is further configured to communicate the event data to i) at least one further transceiver $190_{p,q}$ and/or ii) a computer readable storage medium and/or iii) a reconstruction processor 200. The transceiver therefore facilitates the communication of the event data between the compute elements. The transceiver may for example be provided by an FPGA, or another integrated circuit. The compute elements may consequently perform operations on the event data such as clustering the event data, identifying coincident pairs, or storing the event data.

Figures 4, 5:
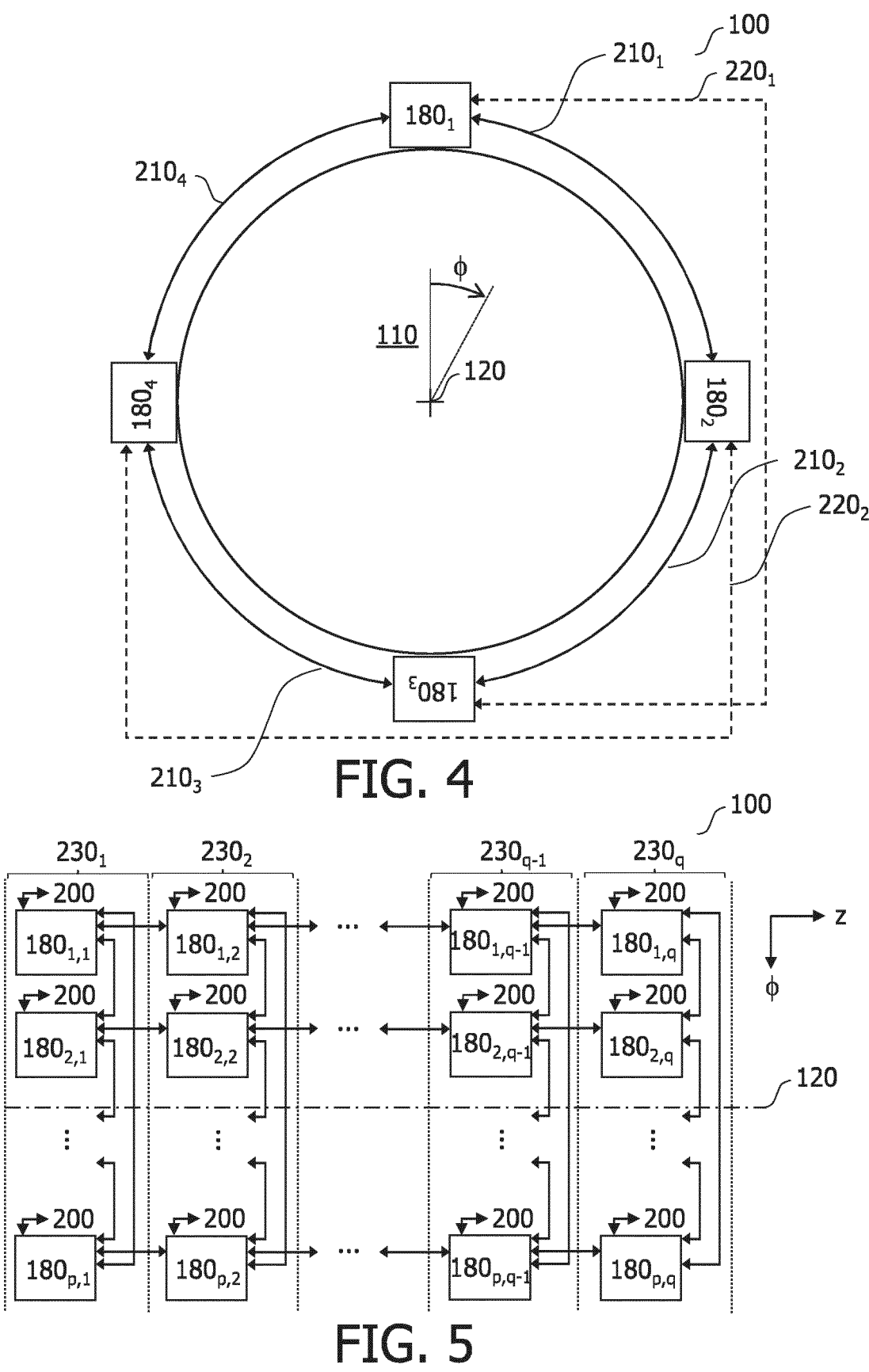
FIG. 4 is a schematic diagram illustrating an example PET imaging system 100 in which a plurality of module elements $180_p$ each include a first module communication path $210_{1..p}$ coupling the module element to an adjacent module element in a circumferential direction around the bore 110, and a second module communication path $220_{1..p}$ coupling the module element to a non-adjacent module element in the circumferential direction, in accordance with some aspects of the present disclosure.
FIG. 5 is a schematic diagram illustrating an example PET imaging system 100 including a plurality of module elements $180_{p,q}$ that are arranged in a plurality of rings $230_{1..q}$, in accordance with some aspects of the present disclosure.

In some examples, the module elements are also arranged around the axis of the bore of the PET imaging system and connected to one another in a similar manner to the compute elements. FIG. 4 is a schematic diagram illustrating an example PET imaging system 100 in which a plurality of module elements $180_p$ each include a first module communication path $210_{1..p}$ coupling the module element to an adjacent module element in a circumferential direction around the bore 110, and a second module communication path $220_{1..p}$ coupling the module element to a non-adjacent module element in the circumferential direction, in accordance with some aspects of the present disclosure. In the example illustrated in FIG. 4, the module elements $180_{p,q}$ are arranged around the axis 120 of the bore 110. Thus, in this example, the module elements are arranged at different rotational angles f around the axis 120. Moreover, the transceiver $190_{p,q}$ of each module element $180_{p,q}$ comprises a first module communication path $210_{1..p}$ coupling the module element to an adjacent module element in a circumferential direction around the bore, and a second module communication path $220_{1..p}$ coupling the module element to a non-adjacent module element in the circumferential direction. The transceiver $190_{p,q}$ of each module element $180_{p,q}$ is configured to communicate the event data generated by the one or more detector elements $130_{1..i}$, $130_{1..i,1..q}$ of its compute elements $140_{1..j}$, $140_{1..j,1..q}$ to the transceiver $190_{p,q}$ of its adjacent module element and to the transceiver of its non-adjacent module element via its first module communication path $210_{1..p}$, and via its second module communication path $220_{1..p}$, respectively.

In so doing, the module communication paths $220_{1..p}$ permit the transfer of event data around the axis of the bore between the compute elements with reduced latency. In some examples, the module communication paths are dynamically selectable by the processors, and thereby offer the ability to circumvent any bandwidth bottlenecks in the first and second communication paths 160, $170_j$ between the compute elements $140_j$. The system architecture provided by this arrangement may also be readily scaled to support additional numbers of detector elements without performance degradation. For example, using this modular arrangement, a PET imaging system with a longer axial field of view may be provided by simply increasing the number of modules. Since the modules have their own communication paths, the available bandwidth increases proportionately, obviating a performance reduction that might otherwise result from re-using existing communication paths for the additional detector elements.

When the module elements are arranged in multiple rings, the module elements may also include module communication paths between adjacent module elements in adjacent rings for transferring event data between the module elements in different rings. This is illustrated in FIG. 5, which is a schematic diagram illustrating an example PET imaging system 100 including a plurality of module elements $180_{p,q}$ that are arranged in a plurality of rings $230_{1..q}$, in accordance with some aspects of the present disclosure. The module communication paths between the different rings may help to reduce the latency of transferring event data between the compute elements by providing an alternative route to the existing communication paths between the compute elements described above.

In some examples, the module element may also provide at least one of the following:

a mechanical support for the plurality of compute elements $140_{1..j}$, $140_{1..j,1..q}$ of the module element $180_{p,q}$; and a mechanical support for the one or more detector elements $130_{1..i}$, $130_{1..i,1..q}$ of the plurality of compute elements $140_{1..j}$, $140_{1..j,1..q}$ of the module element $180_{p,q}$;

a power supply for the plurality of compute elements $140_{1..j}$, $140_{1..j,1..q}$ and/or detector elements $130_{1..i}$, $130_{1..i,1..q}$ of the module element $180_{p,q}$;

a cooling device for cooling the plurality of compute elements $140_{1..j}$, $140_{1..j,1..q}$ and/or detector elements $130_{1..i}$, $130_{1..i,1..q}$ of the module element $180_{p,q}$;

a buffer for storing the event data transmitted and/or received by the transceiver $190_{p,q}$ of the module element $180_{p,q}$.

An important consideration in PET imaging systems is the accuracy with which the detection times of received gamma quanta are determined. Any errors in the detection times may result in the inaccurate determination of coincident events, and lead to poor quality PET images. In accordance with some examples, a hierarchy of reference clock units is provided for use in a PET imaging system. These examples are described with reference to module elements that each include a reference clock unit. It is noted that the reference clock units may instead be located in the detector elements. It is also noted that the reference clock units may be used in the PET imaging system 100 in combination with, or independently from the first and second communication paths described above.

Figure 6:
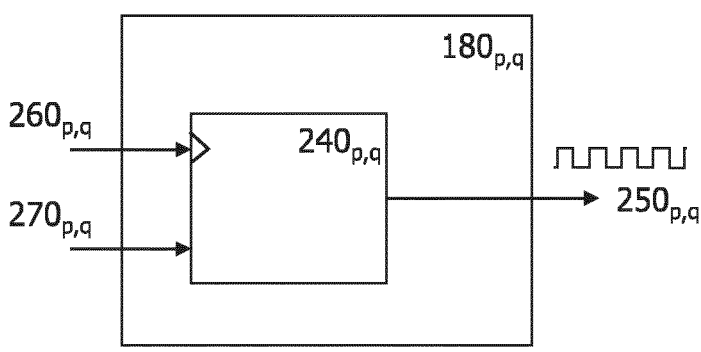
FIG. 6 is a schematic diagram illustrating an example of a reference clock unit $240_{p,q}$, in accordance with some aspects of the present disclosure.

FIG. 6 is a schematic diagram illustrating an example of a reference clock unit $240_{p,q}$, in accordance with some aspects of the present disclosure. In FIG. 6 the example reference clock unit $240_{p,q}$ is included in a module element $180_{p,q}$, although as mentioned above, the reference clock unit $240_{p,q}$ may alternatively be included in a compute element. The reference clock unit $240_{p,q}$ includes an output $250_{p,q}$ that generates a clock signal, a synchronization input $260_{p,q}$ that can receives a clock signal from another reference clock unit, and a control input $270_{p,q}$ for selecting the reference clock unit to operate as a master clock for generating clock signals for another reference clock unit or as a slave clock for generating clock signals based on a received clock signal from another reference clock unit. Various known integrated circuits may be used to provide the reference clock unit $240_{p,q}$.

Figure 7:
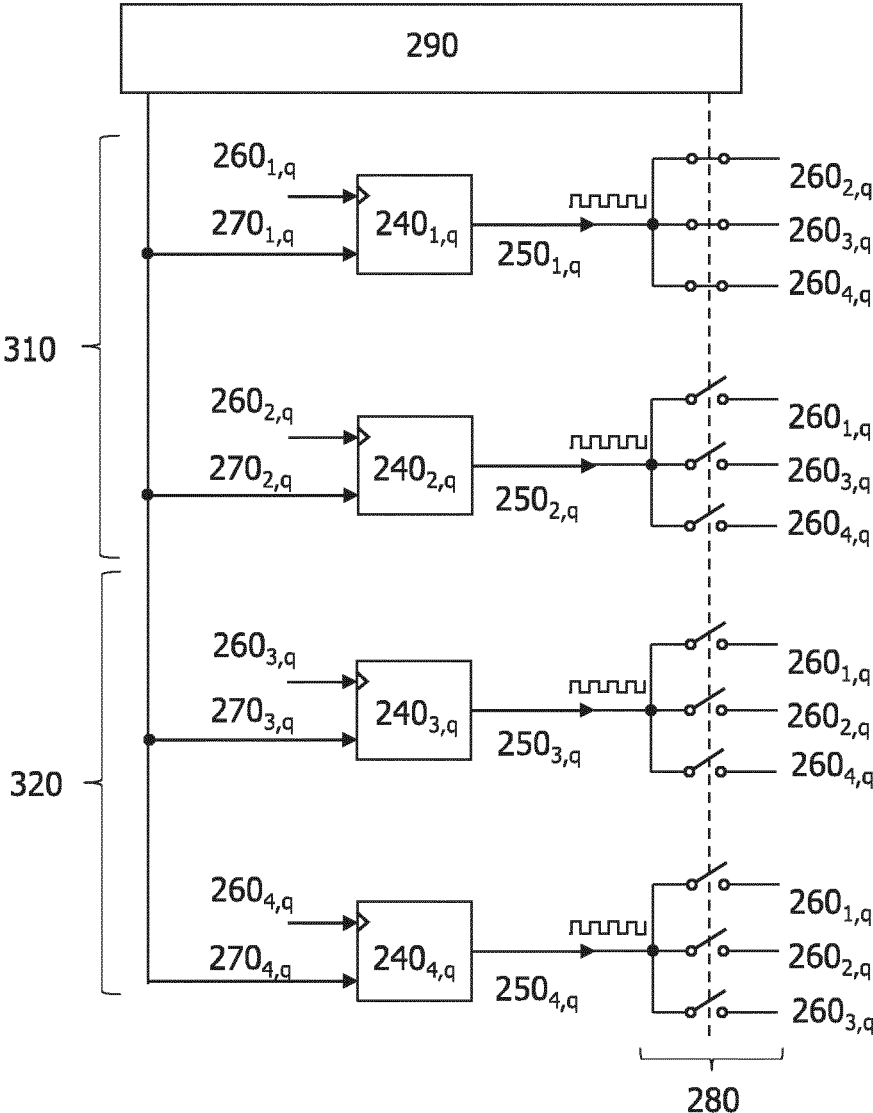
FIG. 7 is a schematic diagram illustrating an example of a clock hierarchy with a plurality of reference clock units at a primary level 310 of the hierarchy, and a plurality of reference clock units at a secondary level 320 of the hierarchy, in accordance with some aspects of the present disclosure.

The example reference clock unit illustrated in FIG. 6 may be arranged in a hierarchy and included in the PET imaging system 100 described above. FIG. 7 is a schematic diagram illustrating an example of a clock hierarchy with a plurality of reference clock units at a primary level 310 of the hierarchy, and a plurality of reference clock units at a secondary level 320 of the hierarchy, in accordance with some aspects of the present disclosure. With reference to FIG. 7, in this example, each compute element $140_{1..j}$ or each module element $180_{p,q}$ of the PET imaging system 100 comprises a reference clock unit $240_{p,q}$ for determining detection times of gamma quanta $150_a$, $150_b$ received by the detector elements $130_{1..i}$. Each reference clock unit $240_{p,q}$ comprises an output $250_{p,q}$ configured to generate a clock signal, a synchronization input $260_{p,q}$ configured to receive a clock signal from another reference clock unit, and a control input $270_{p,q}$ for selecting the reference clock unit to operate as a master clock for generating clock signals for another reference clock unit or as a slave clock for generating clock signals based on a received clock signal from another reference clock unit. The outputs $250_{p,q}$ and the synchronization inputs $260_{p,q}$ of the reference clock units include a reconfigurable interconnect 280 for providing a clock hierarchy with a plurality of reference clock units at a primary level 310 of the hierarchy, and a plurality of reference clock units at a secondary level 320 of the hierarchy, the primary level of the hierarchy including a reference clock unit operating as a master clock, and one or more reference clock units operating as slave clocks, and the secondary level of the hierarchy including a plurality of reference clock units operating as slave clocks. Moreover, each reference clock unit is selectively controllable via its control input and its reconfigurable interconnect to operate at the primary level of the hierarchy or at the secondary level of the hierarchy.

The hierarchy illustrated in FIG. 7 is adaptable by means of the reconfigurable interconnect 280 and the control inputs $270_{p,q}$. In the illustrated example, the reconfigurable interconnect includes a plurality of switches that are controlled by an interconnect controller 290 to provide the desired connections between the outputs $250_{p,q}$ and the synchronization inputs $260_{p,q}$ of the reference clock units. The switches of the reconfigurable interconnect 280 may be provided by transistor switches. The switches may be addressed and set, as desired, to open or closed, as in a multiplexer. The reconfigurable interconnect 280 permits any of the reference clock units to operate as master clock, or alternatively as a slave clock.

By providing each compute element $140_{1..j}$ or each module element $180_{p,q}$ of the PET imaging system 100 with a reference clock in this manner, the PET imaging system incorporates redundancy, thereby allowing the PET imaging system to operate more reliably. Accurate times of detection of the gamma quanta can also be obtained because the clocks are driven by a common master clock.

In accordance with one example, the reference clock units $240_{p,q}$ are distributed around the axis 120 of the bore 110 of the PET imaging system, and selectively controlled by their control inputs $270_{p,q}$ and their reconfigurable interconnect 280 such that:

a plurality of the secondary-level reference clock units 320 are disposed on both sides of each of the primary-level reference clock units 310;

the outputs $250_{p,q}$ and the synchronization inputs $260_{p,q}$ of the primary-level reference clock units 310 are interconnected such that the output of the reference clock unit operating as the master clock is inputted into the one or more synchronization inputs of the one or more reference clock units operating as slave clocks; and the synchronization inputs $260_{p,q}$ of the secondary-level reference clock units 320 are interconnected to the output $250_{p,q}$ of their nearest primary-level reference clock unit 310 for receiving a clock signal from the output of their nearest primary-level reference clock unit 310.

Figures 8, 9, 10:
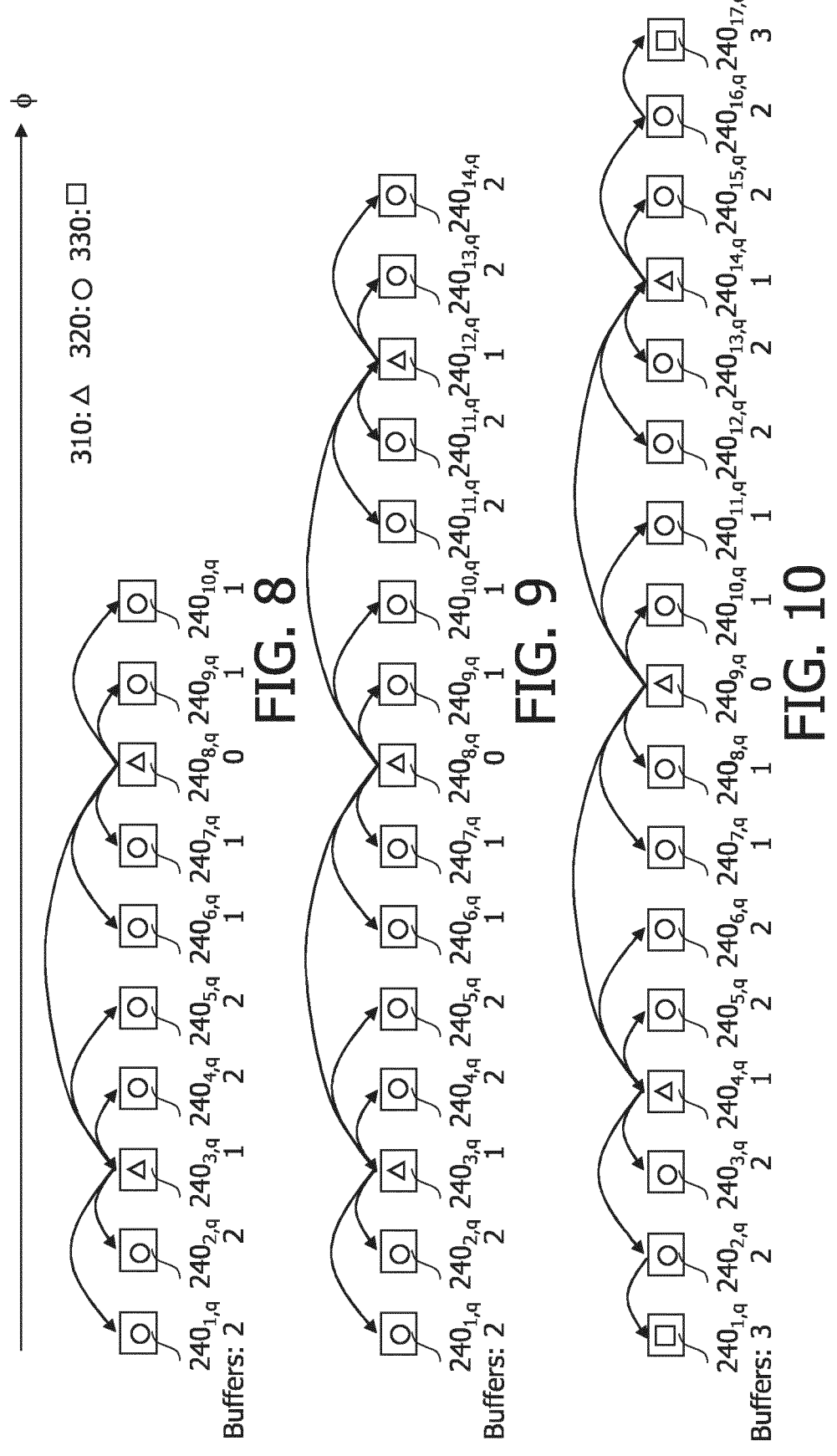
FIG. 8 is a schematic diagram illustrating a first example of a distribution of reference clock units $240_{p,q}$ around the axis of the bore of a PET imaging system, in accordance with some aspects of the present disclosure.
FIG. 9 is a schematic diagram illustrating a second example of a distribution of reference clock units $240_{p,q}$ around the axis of the bore of a PET imaging system, in accordance with some aspects of the present disclosure.
FIG. 10 is a schematic diagram illustrating a third example of a distribution of reference clock units $240_{p,q}$ around the axis of the bore of a PET imaging system, in accordance with some aspects of the present disclosure.

This distribution of the reference clock units permits the clock signal from the master clock to be distributed around the bore of the PET imaging system with low jitter, or in other words, high timing accuracy. Moreover, the interconnect 280 is reconfigurable, and so this arrangement incorporates redundancy, allowing the PET imaging system to operate reliably. FIG. 8 to FIG. 10 illustrate various examples of distributions of reference clock units $240_{p,q}$ around the axis of the bore of a PET imaging system, in accordance with this principle. In FIG. 8 to FIG. 10, symbol f represents the rotational angle around the axis 120 of the bore 110 of the PET imaging system, and corresponds to rotational angle f in FIG. 1. The triangle, circle, and square symbol represent primary-level reference clock units 310, secondary-level reference clock unit 320, and third-level reference clock unit 330, respectively. The "Buffers" label indicates the number of buffers that the master clock signal may pass through in order to arrive at the respective reference clock unit. The clock signal may be buffered by virtue of being outputted by another reference clock unit. Although not illustrated, the reference clock units typically include a buffer for this purpose. Each time the master clock signal passes through such a buffer, it adds a delay to the clock signal. Thus, it is desirable to distribute the master clock signal around the bore of the PET imaging system with a low number of buffers.

FIG. 8 is a schematic diagram illustrating a first example of a distribution of reference clock units $240_{p,q}$ around the axis of the bore of a PET imaging system, in accordance with some aspects of the present disclosure. In the example illustrated in FIG. 8, there are p=10 reference clock units, and q rings are distributed axially along the axis 120 of the bore 110. In other examples, there may alternatively be a different number of reference clock units, and also only a single ring, q. When multiple rings are used, each reference clock units in one ring may be further coupled to a reference clock unit in an adjacent ring. In FIG. 8, the reference clock units $240_{3,q}$ and $240_{8,q}$ operate as primary-level reference clock units 310, and the reference clock unit $240_{8,q}$ serves as the master clock. The clock signals generated by the reference clock unit $240_{8,q}$; i.e. the master clock, are inputted into the reference clock unit $240_{3,q}$, as well as into the reference clock unit $240_{6,q}$ and $240_{7,q}$ and $240_{9,q}$ and $240_{10,q}$; the latter operating as secondary-level reference clock units 320. From the reference clock unit $240_{3,q}$, the clock signal is further distributed to the reference clock unit $240_{1,q}$ and $240_{2,q}$ and $240_{4,q}$ and $240_{5,q}$. The arrangement illustrated in FIG. 8 has been found to provide low jitter due to the low number of buffers ("Buffers" label in FIG. 8 to FIG. 10) between the master clock and the reference clock units. By contrast, a daisy-chain arrangement of reference clock units would rapidly accumulate jitter along the chain. The arrangement illustrated in FIG. 8 is also capable of being scaled to additional numbers of reference clock units whilst maintaining a common wiring infrastructure, as seen in the sequence of Figures from FIG. 8 to FIG. 10.

FIG. 9 is a schematic diagram illustrating a second example of a distribution of reference clock units $240_{p,q}$ around the axis of the bore of a PET imaging system, in accordance with some aspects of the present disclosure. As compared to FIG. 8, the distribution illustrated in FIG. 9 includes additional reference clock units, demonstrating its scalability to additional numbers of reference clock units whilst maintaining a common wiring infrastructure. FIG. 10 is a schematic diagram illustrating a third example of a distribution of reference clock units $240_{p,q}$ around the axis of the bore of a PET imaging system, in accordance with some aspects of the present disclosure. As compared to FIG. 8 and FIG. 9, FIG. 10 includes an additional layer in the hierarchy, and wherein the reference clock units $240_{1,q}$ and $240_{17,q}$ operate as third-level reference clock units 330. In FIG. 10, the distribution of the reference clock units results in a non-uniform skew, which is advantageous since it results in reduced electromagnetic interference by avoiding simultaneous switching of the reference clock units. Other distributions of the reference clock units may also be used that follow the same principles.

The above examples are to be understood as illustrative of the present disclosure, and not restrictive. Further examples are also contemplated. It is to be understood that a feature described in relation to any one example may be used alone, or in combination with other described features, and may be used in combination with one or more features of another of the examples, or a combination of other examples. Furthermore, equivalents and modifications not described above may also be employed without departing from the scope of the invention, which is defined in the accompanying claims. In the claims, the word "comprising" does not exclude other elements or operations, and the indefinite article "a" or "an" does not exclude a plurality. The mere fact that certain features are recited in mutually different dependent claims does not indicate that a combination of these features cannot be used to advantage. Any reference signs in the claims should not be construed as limiting their scope.

The invention claimed is:

1. A positron emission tomography imaging system comprising:

a bore for receiving a subject, the bore comprising an axis;

a plurality of detector elements; and a plurality of compute elements;

wherein each detector element comprises a scintillator array coupled to a photodetector array, and is configured to generate event data in response to received gamma quanta, the event data representing detection times of the received gamma quanta and/or a light distribution generated in the scintillator array in response to the received gamma quanta;

wherein each compute element comprises one or more of the detector elements, and wherein the compute elements are arranged around the axis of the bore such that the detector elements generate the event data in response to gamma quanta received from within the bore;

wherein each compute element comprises a first communication path coupling the compute element to an adjacent compute element in a circumferential direction around the bore, and a second communication path coupling the compute element to a non-adjacent compute element in the circumferential direction; and wherein each compute element comprises a processor configured to receive the event data generated by its one or more detector elements, and to communicate the event data to the processor of its adjacent compute element, and to the processor of its non-adjacent compute element, via its first communication path, and via its second communication path, respectively.

2. The positron emission tomography imaging system according to claim 1, wherein the compute elements are grouped to define a plurality of module elements;

wherein each module element comprises a plurality of the compute elements and a transceiver; and wherein the transceiver of each module element is in communication with the compute elements of the module element, and configured to receive the event data generated by the one or more detector elements of the compute elements of the module element; and wherein the transceiver of each module element is further configured to communicate the event data to i) at least one further transceiver and/or ii) a computer readable storage medium and/or iii) a reconstruction processor.

3. The positron emission tomography imaging system according to claim 2, wherein the module elements are arranged around the axis of the bore;

wherein the transceiver of each module element comprises a first module communication path coupling the module element to an adjacent module element in a circumferential direction around the bore, and a second module communication path coupling the module element to a non-adjacent module element in the circumferential direction; and wherein the transceiver of each module element is configured to communicate the event data generated by the one or more detector elements of its compute elements to the transceiver of its adjacent module element and to the transceiver of its non-adjacent module element via its first module communication path, and via its second module communication path, respectively.

4. The positron emission tomography imaging system according to claim 2, wherein each module element is further configured to provide at least one of the following:

a mechanical support for the plurality of compute elements of the module element; and a mechanical support for the one or more detector elements of the plurality of compute elements of the module element;

or wherein each module element further comprises:

a power supply for the plurality of compute elements and/or detector elements of the module element;

a cooling device for cooling the plurality of compute elements and/or detector elements of the module element;

a buffer for storing the event data transmitted and/or received by the transceiver of the module element.

5. The positron emission tomography imaging system according to claim 1, wherein the compute elements are arranged in a plurality of rings;

wherein the rings are distributed axially along the axis of the bore; and wherein the processor of each compute element in a ring is further configured to communicate the event data to the processor of an adjacent compute element in an adjacent ring.

6. The positron emission tomography imaging system according to claim 1, wherein the processor of each compute element is further configured to:

cluster the event data by assigning the light distribution generated in one or more scintillator arrays to a common received gamma quant; and/or identify coincident pairs of received gamma quanta having detection times within a predetermined time interval of one another.

7. The positron emission tomography imaging system according to claim 6, wherein the processor of each compute element is configured to cluster the event data by assigning the light distribution generated in one or more scintillator arrays of a detector element of the compute element, and/or the light distribution generated in one or more scintillator arrays of a detector element of an adjacent compute element, to a common received gamma quant; and/or wherein the processor of each compute element is further configured to compute a total energy of the received gamma quant based on the cluster; and/or wherein the processor of each compute element is further configured to determine a position of the received gamma quant based on the cluster.

8. The positron emission tomography imaging system according to claim 6, wherein the processor of each compute element is configured to identify coincident pairs of received gamma quanta having detection times within a predetermined time interval of one another by:

comparing the detection time of a gamma quant detected by a detector element of the compute element, with the detection times of one or more other gamma quanta detected by other detector elements of other compute elements to identify a corresponding gamma quant having a detection time within the predetermined time interval.

9. The positron emission tomography imaging system according to claim 8, wherein the processor of each compute element is further configured to:

identify, based on the comparing, a corresponding compute element of the detector element detecting the corresponding gamma quant; and to transmit the event data of the detected gamma quant to the processor of the corresponding compute element, and/or receive the event data of the corresponding gamma quant from the other compute element.

10. The positron emission tomography imaging system according to claim 9, wherein the processor of each compute element is further configured to communicate the event data for the coincident pairs to i) a computer readable storage medium and/or ii) a reconstruction processor.

11. The positron emission tomography imaging system according to claim 1, wherein the processor of each compute element is configured to transmit the event data generated by its one or more detector elements to the processor of its adjacent compute element and to the processor of its non-adjacent compute element via its first communication path and via its second communication path, respectively; and wherein the processor of each compute element is further configured to receive event data from the processor of its adjacent compute element, and from the processor of its non-adjacent compute element via its first communication path and via its second communication path, respectively.

12. The positron emission tomography imaging system according to claim 11, wherein each compute element is further configured to receive a control signal for switching operation of each compute element between i) transmitting the event data generated by its one or more detector elements to the processor of its adjacent compute element and to the processor of its non-adjacent compute element, and ii) receiving event data from the processor of its adjacent compute element, and from the processor of its non-adjacent compute element.

13. The positron emission tomography imaging system according to claim 1, wherein each detector element and/or each compute element comprises a buffer for storing the event data.

14. The positron emission tomography imaging system according to claim 1, wherein each compute element or each module element comprises a reference clock unit for determining detection times of gamma quanta received by the detector elements;

wherein each reference clock unit comprises an output configured to generate a clock signal, a synchronization input configured to receive a clock signal from another reference clock unit, and a control input for selecting the reference clock unit to operate as a master clock for generating clock signals for another reference clock unit or as a slave clock for generating clock signals based on a received clock signal from another reference clock unit;

wherein the outputs and the synchronization inputs of the reference clock units include a reconfigurable interconnect for providing a clock hierarchy with a plurality of reference clock units at a primary level of the hierarchy, and a plurality of reference clock units at a secondary level of the hierarchy, the primary level of the hierarchy including a reference clock unit operating as a master clock, and one or more reference clock units operating as slave clocks, and the secondary level of the hierarchy including a plurality of reference clock units operating as slave clocks; and wherein each reference clock unit is selectively controllable via its control input and its reconfigurable interconnect to operate at the primary level of the hierarchy or at the secondary level of the hierarchy.

15. The positron emission tomography imaging system according to claim 14, wherein the reference clock units are distributed around the axis of the bore, and selectively controlled by their control inputs and their reconfigurable interconnect such that:

a plurality of the secondary-level reference clock units are disposed on both sides of each of the primary-level reference clock units;

the outputs and the synchronization inputs of the primary-level reference clock units are interconnected such that the output of the reference clock unit operating as the master clock is inputted into the one or more synchronization inputs of the one or more reference clock units operating as slave clocks; and the synchronization inputs of the secondary-level reference clock units are interconnected to the output of their nearest primary-level reference clock unit for receiving a clock signal from the output of their nearest primary-level reference clock unit.

\* \* \* \* \*